(12) United States Patent
Ehrnsperger et al.

(10) Patent No.: US 10,952,909 B2
(45) Date of Patent: Mar. 23, 2021

(54) ABSORBENT CORES FOR ABSORBENT ARTICLES

(71) Applicant: The Procter & Gamble Company, Cincinnati, OH (US)

(72) Inventors: Bruno Johannes Ehrnsperger, Bad Soden (DE); Hans Adolf Jackels, Mechernich (DE); Claus Peter Stoelzel, Bad Soden (DE); Christine Elisabeth Zipf, Lauda-Königshofen (DE)

(73) Assignee: The Procter & Gamble Company, Cincinnati, OH (US)

(*) Notice: Subject to any disclaimer, the term of this patent is extended or adjusted under 35 U.S.C. 154(b) by 603 days.

(21) Appl. No.: 15/044,164

(22) Filed: Feb. 16, 2016

(65) Prior Publication Data
US 2016/0235595 A1 Aug. 18, 2016

(30) Foreign Application Priority Data
Feb. 17, 2015 (EP) .................................. 15155439

(51) Int. Cl.
*A61F 13/49* (2006.01)
*A61F 13/539* (2006.01)
(Continued)

(52) U.S. Cl.
CPC ...... *A61F 13/49001* (2013.01); *A61F 13/535* (2013.01); *A61F 13/536* (2013.01);
(Continued)

(58) Field of Classification Search
CPC ............... A61F 13/49001; A61F 13/49; A61F 13/00017; A61F 13/4704; A61F 13/475;
(Continued)

(56) References Cited

U.S. PATENT DOCUMENTS 3,744,494 A * 7/1973 Marsan ............. A61F 13/53409
604/378
3,860,003 A 1/1975 Buell
(Continued)

FOREIGN PATENT DOCUMENTS

EP        149880       7/1985
EP      0241041     10/1987
(Continued)

OTHER PUBLICATIONS

Mei Ziqiang, "Dictionary of Textiles", China Textile Press, Jan. 2007, p. 552. (Official Language only).
(Continued)

*Primary Examiner* — Bradley H Philips
*Assistant Examiner* — Cana A Gallegos
(74) *Attorney, Agent, or Firm* — Wednesday G. Shipp

(57) ABSTRACT

An absorbent core includes a core wrap having a top layer and a bottom layer enclosing superabsorbent polymer. The absorbent core is substantially free of cellulose fibers. The absorbent layer comprises a non-rectangular central portion having a front edge, a back edge and two longitudinally-extending side edges. Each side edge defines a recess along a portion of its length; a first side portion present in one of the recess and a second side portion present in the other recess. The proximal edges of the side portions are convex; and either the distal edges of the side portions are concave so that the side portions are crescent-shaped; or the distal edges of the side portions is straight. The absorbent core further includes a first and second folding guide, and when the absorbent core is folded along the folding guides, the central portion and the side portions form a three-dimensional basin.

7 Claims, 7 Drawing Sheets

(51) Int. Cl.
  *A61F 13/535* (2006.01)
  *A61F 13/536* (2006.01)
  *A61F 13/531* (2006.01)
  *A61F 13/53* (2006.01)

(52) U.S. Cl.
  CPC .... *A61F 13/539* (2013.01); *A61F 2013/5315* (2013.01); *A61F 2013/530481* (2013.01); *A61F 2013/53908* (2013.01)

(58) Field of Classification Search
  CPC .. A61F 13/539; A61F 13/537; A61F 13/4757; A61F 13/47236
  See application file for complete search history.

(56) References Cited

U.S. PATENT DOCUMENTS

| | | |
|---|---|---|
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,609,518 A | 9/1986 | Curro et al. |
| 4,629,643 A | 12/1986 | Curro et al. |
| 4,695,278 A | 9/1987 | Lawson |
| 4,762,521 A | 8/1988 | Roessler et al. |
| 4,795,454 A | 1/1989 | Dragoo |
| 4,808,178 A | 2/1989 | Aziz et al. |
| 4,909,803 A | 3/1990 | Aziz et al. |
| 5,006,394 A | 4/1991 | Baird |
| 5,137,537 A | 8/1992 | Herron et al. |
| 5,221,274 A | 6/1993 | Buell et al. |
| 5,554,145 A | 9/1996 | Roe et al. |
| 5,569,234 A | 10/1996 | Buell et al. |
| 5,580,411 A | 12/1996 | Nease et al. |
| 5,607,760 A | 3/1997 | Roe |
| 5,609,587 A | 3/1997 | Roe |
| 5,643,588 A | 7/1997 | Roe et al. |
| 5,700,254 A | 12/1997 | McDowall et al. |
| 5,792,130 A * | 8/1998 | Widlund ............ A61F 13/4946 604/385.01 |
| 5,968,025 A | 10/1999 | Roe et al. |
| 5,971,153 A | 10/1999 | Bauer |
| 6,004,306 A | 12/1999 | Robles et al. |
| 6,328,724 B1 | 12/2001 | Ronnberg et al. |
| 6,420,627 B1 | 7/2002 | Ohnishi |
| 6,520,945 B1 * | 2/2003 | Hansson ............ A61F 13/4702 604/385.24 |
| 6,632,504 B1 | 10/2003 | Gillespie et al. |
| 6,645,569 B2 | 11/2003 | Cramer et al. |
| 6,689,933 B1 | 2/2004 | Dipalma |
| 6,716,441 B1 | 4/2004 | Roe et al. |
| 6,863,933 B2 | 3/2005 | Cramer et al. |
| 7,008,408 B2 * | 3/2006 | Otsubo ............ A61F 13/49426 604/385.01 |
| 7,112,621 B2 | 9/2006 | Rohrbaugh et al. |
| 7,169,136 B2 | 1/2007 | Otsubo et al. |
| 7,220,251 B2 | 5/2007 | Otsubo |
| 7,329,246 B2 | 2/2008 | Kinoshita et al. |
| 7,588,561 B2 | 9/2009 | Kenmochi et al. |
| 7,732,039 B2 | 6/2010 | Chavravarty et al. |
| 7,744,576 B2 | 6/2010 | Busam et al. |
| 9,789,009 B2 * | 10/2017 | Joseph ............ A61F 13/42 |
| 10,137,040 B2 | 11/2018 | Ehrnsperger |
| 10,456,305 B2 | 10/2019 | Ehrnsperger |
| 2001/0056271 A1 | 12/2001 | Shingu |
| 2002/0028858 A1 | 3/2002 | Diehl et al. |
| 2002/0087140 A1 * | 7/2002 | Otsubo ............ A61F 13/4946 604/385.28 |
| 2002/0151861 A1 | 10/2002 | Klemp |
| 2003/0105190 A1 | 6/2003 | Diehl et al. |
| 2003/0148684 A1 | 8/2003 | Cramer et al. |
| 2004/0068244 A1 | 4/2004 | Salone |
| 2004/0243078 A1 | 12/2004 | Guidotti et al. |
| 2005/0008839 A1 | 1/2005 | Cramer et al. |
| 2005/0033252 A1 | 2/2005 | Schneider et al. |
| 2005/0033253 A1 | 2/2005 | Fuchs et al. |
| 2005/0043694 A1 | 2/2005 | Schneider et al. |
| 2005/0143711 A1 | 6/2005 | Otsubo |
| 2005/0148970 A1 | 7/2005 | Kudo |
| 2006/0004334 A1 | 1/2006 | Schlinz et al. |
| 2006/0024433 A1 | 2/2006 | Blessing et al. |
| 2006/0040579 A1 | 2/2006 | Sheldon |
| 2006/0184146 A1 | 8/2006 | Suzuki |
| 2007/0244455 A1 * | 10/2007 | Hansson ............ A61F 13/4704 604/385.201 |
| 2008/0119810 A1 | 5/2008 | Kuroda |
| 2008/0312617 A1 | 12/2008 | Hundorf et al. |
| 2008/0312622 A1 | 12/2008 | Hundorf et al. |
| 2008/0312624 A1 | 12/2008 | Hundorf |
| 2008/0312625 A1 | 12/2008 | Hundorf et al. |
| 2008/0312627 A1 | 12/2008 | Takeuchi et al. |
| 2009/0112175 A1 | 4/2009 | Bissah |
| 2010/0051166 A1 | 3/2010 | Hundorf et al. |
| 2011/0073513 A1 | 3/2011 | Weisman et al. |
| 2011/0152813 A1 | 6/2011 | Ellingson |
| 2011/0184364 A1 | 7/2011 | Biggs |
| 2011/0250413 A1 | 10/2011 | Lu et al. |
| 2011/0268932 A1 | 11/2011 | Catalan et al. |
| 2011/0319848 A1 | 12/2011 | McKiernan et al. |
| 2012/0312491 A1 | 12/2012 | Jackels et al. |
| 2012/0316526 A1 * | 12/2012 | Rosati ............ A61F 13/532 604/366 |
| 2012/0316528 A1 | 12/2012 | Kreuzer |
| 2013/0090620 A1 | 4/2013 | Carbonari |
| 2014/0027066 A1 | 1/2014 | Jackels et al. |
| 2014/0163506 A1 * | 6/2014 | Roe ............ A61F 13/49001 604/378 |
| 2015/0173968 A1 | 6/2015 | Joseph |
| 2016/0113825 A1 | 4/2016 | Bianchi |
| 2016/0175168 A1 | 6/2016 | Zink, II |
| 2016/0235594 A1 | 8/2016 | Ehrnsperger |
| 2016/0235596 A1 | 8/2016 | Ehrnsperger |
| 2016/0235597 A1 | 8/2016 | Ehrnsperger |
| 2016/0235602 A1 | 8/2016 | Ehrnsperger |
| 2016/0235603 A1 | 8/2016 | Ehrnsperger et al. |
| 2016/0235604 A1 | 8/2016 | Ehrnsperger |
| 2016/0235605 A1 | 8/2016 | Ehrnsperger |
| 2020/0000647 A1 | 1/2020 | Ehrnsperger |

FOREIGN PATENT DOCUMENTS

| | | |
|---|---|---|
| EP | 2813201 B1 | 11/2017 |
| JP | 2013-000238 A | 1/2013 |
| WO | WO 95/10996 | 4/1995 |
| WO | WO 95/16418 | 6/1995 |
| WO | WO 95/24173 | 9/1995 |
| WO | 9733815 A1 | 9/1997 |
| WO | 9822279 A1 | 5/1998 |
| WO | 0045762 A1 | 8/2000 |
| WO | WO 2000/59430 | 10/2000 |
| WO | WO 02/067809 | 9/2002 |
| WO | 03105738 A1 | 12/2003 |
| WO | WO 2005/105010 | 11/2005 |
| WO | WO 2006/059922 | 6/2006 |
| WO | WO 2006/068549 | 6/2006 |
| WO | WO 2007/069958 | 6/2007 |
| WO | WO 2008/155702 | 12/2008 |
| WO | WO 2008/155722 | 12/2008 |
| WO | WO 2011/041352 | 4/2011 |
| WO | WO 2011/163582 | 12/2011 |
| WO | 2012074466 A1 | 6/2012 |
| WO | WO 2012/170341 | 12/2012 |
| WO | WO 2012/170778 | 12/2012 |
| WO | WO 2012/174026 | 12/2012 |
| WO | WO 2014/078247 | 5/2014 |
| WO | WO 2014/093310 | 6/2014 |

(56) References Cited

FOREIGN PATENT DOCUMENTS

WO  WO 2014/093323     6/2014
WO     2015031229 A1   3/2015

OTHER PUBLICATIONS

"Discovery: Chemistry and Materials Science", Eaglemoss Press, China Peace Publishing House, Jun. 2014, p. 57. (Official Language only).
All Office Actions, U.S. Appl. No. 15/044,138.
All Office Actions, U.S. Appl. No. 15/044,146.
All Office Actions, U.S. Appl. No. 15/044,173.
All Office Actions, U.S. Appl. No. 15/044,183.
All Office Actions, U.S. Appl. No. 16/568,634.
Dictionary.com "To", available at https://www.dictionary.com/browse/to, accessed Oct. 15, 2018.

* cited by examiner

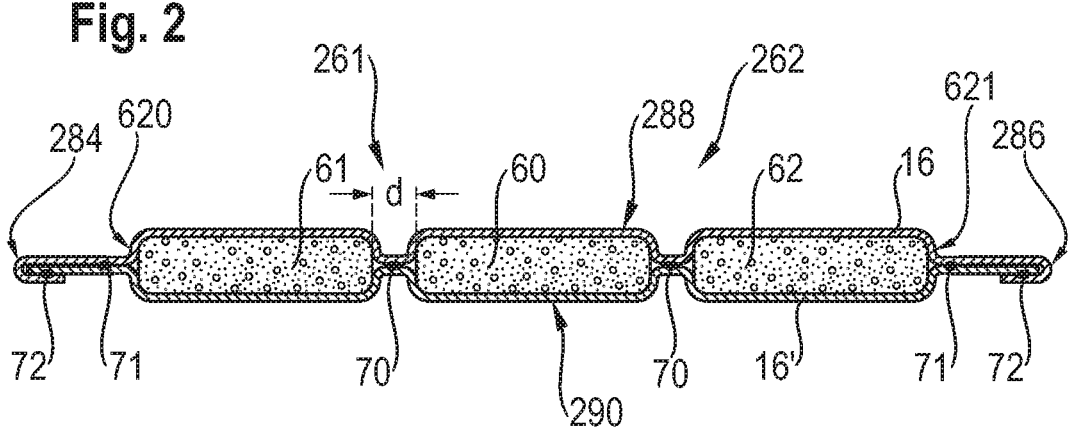
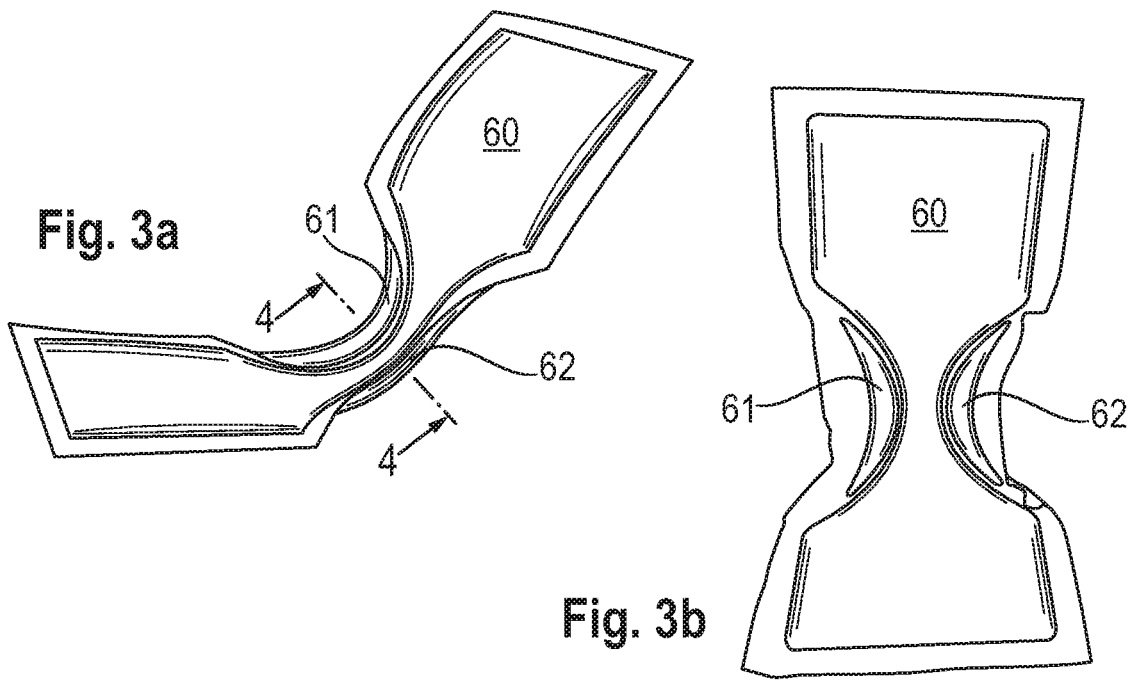
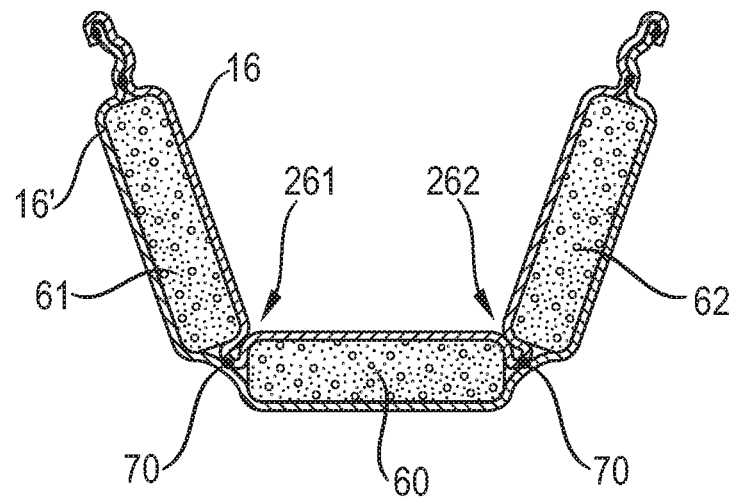

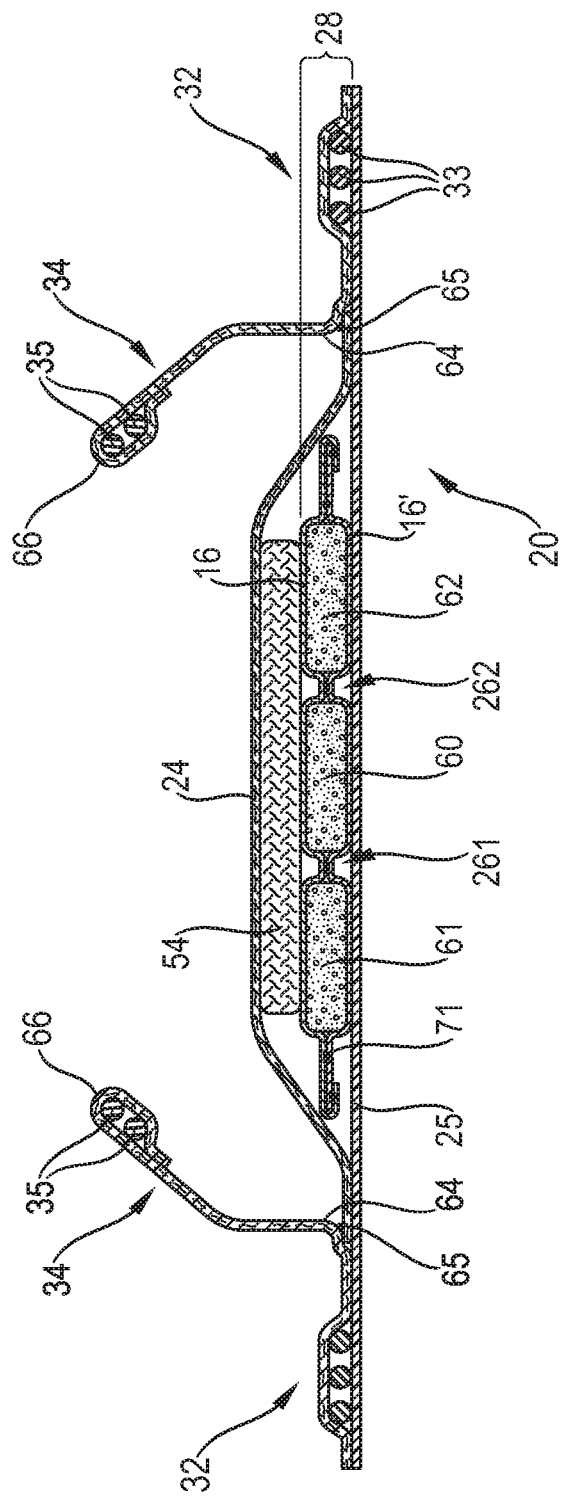

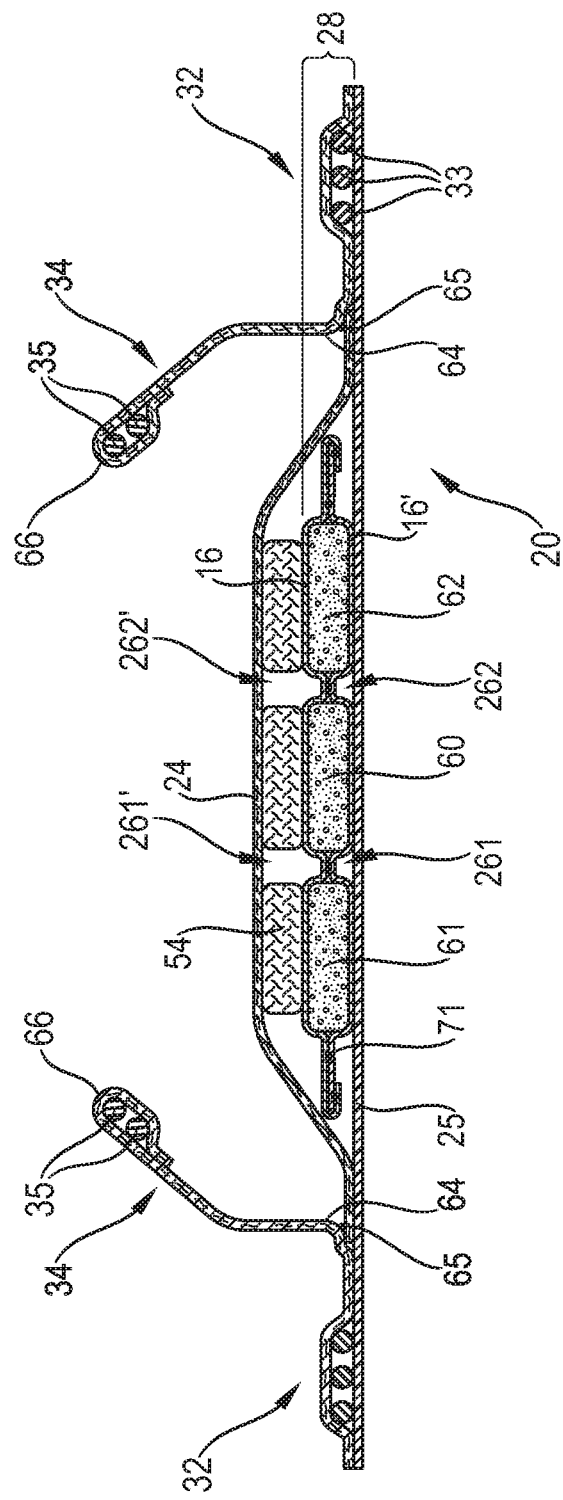

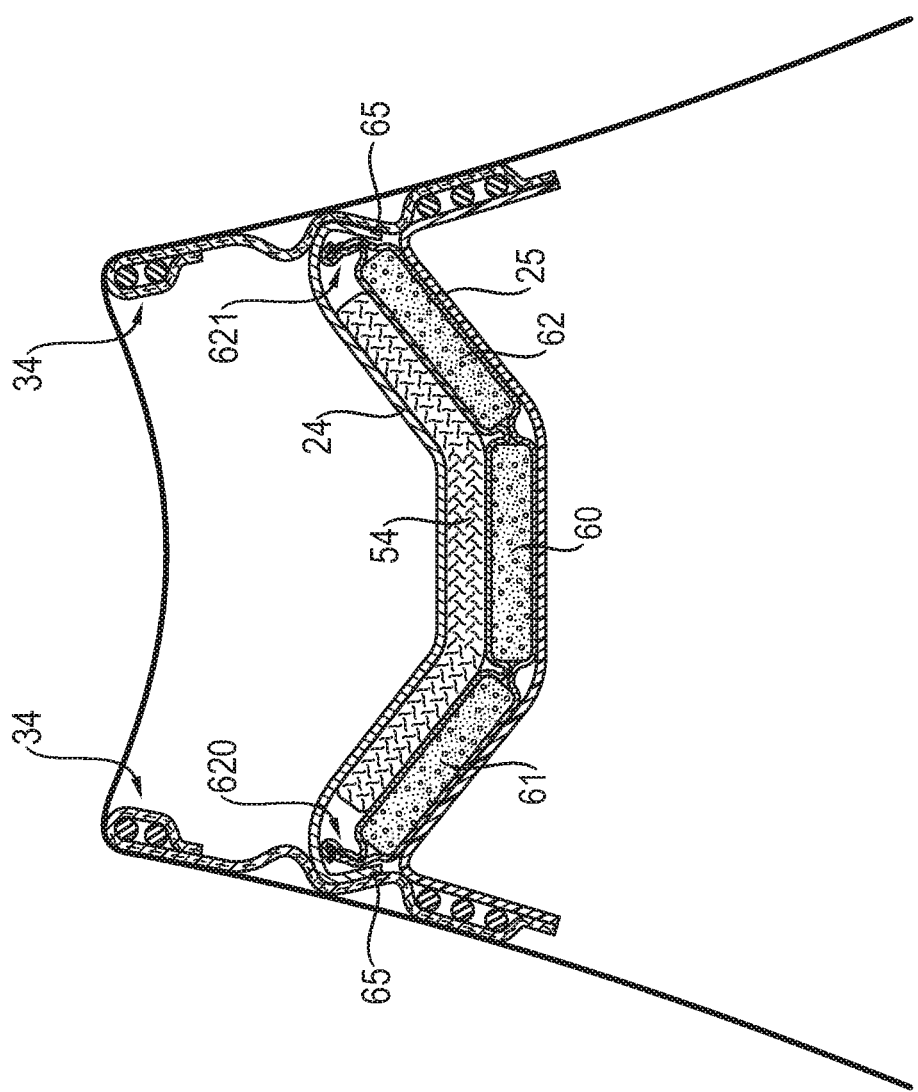

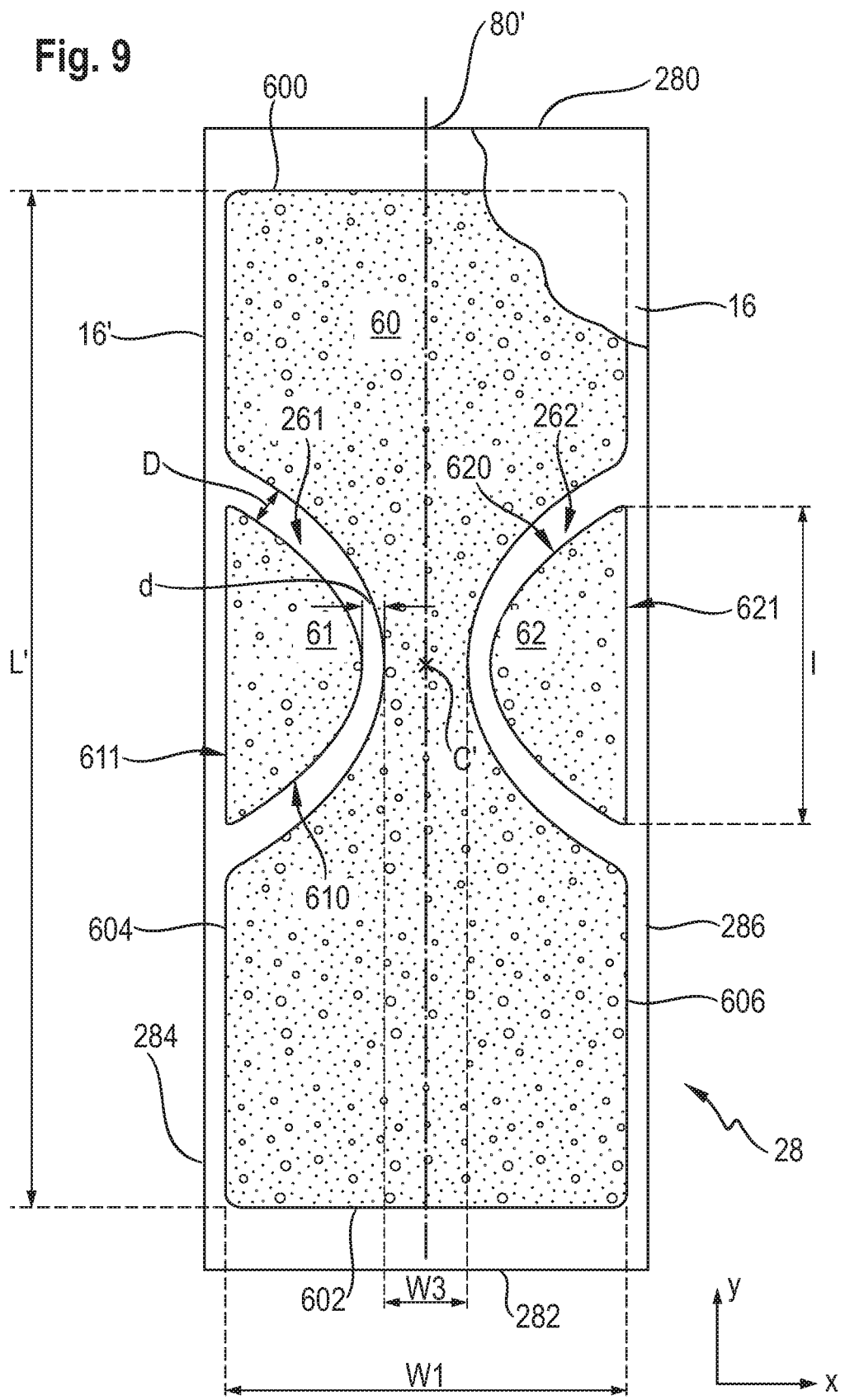

ABSORBENT CORES FOR ABSORBENT ARTICLES

FIELD OF THE INVENTION

The invention relates to absorbent cores for personal hygiene absorbent articles that can be used by an incontinent individual to absorb body exudates such as urine, in particular but not limited to baby diapers and adult incontinence products.

BACKGROUND OF THE INVENTION

Modern diapers typically comprise an absorbent core containing a mixture of cellulose fibers and superabsorbent polymer ("SAP") particles as absorbent material. Over the years, the relative amount of SAP in the absorbent core has increased thus providing thinner absorbent cores. Absorbent articles with an absorbent core material without cellulose fibers, so called airfelt-free cores, have also been recently proposed. Absorbent cores comprising a central portion and two side portions separated by folding guides have also been suggested for providing an improved fit and reduced leakage.

Typically, as absorbent articles become saturated with urine, they tend to sag down in the crotch region of the wearer due to the weight of the fluid. This may cause loss of contact of the article along the thighs of the wearer and increase the possibility of leakages. While elastic waist bands and other elasticized parts such as barrier leg cuffs are commonly used to maintain contact and fit, these solutions are limited and leakage can still occur, especially if the diaper was not put in place correctly or was displaced out of position by the wearer.

Despite the improvements suggested in the prior art, there is a continuous need for improving dry and wet fit, wearing comfort, and fluid handling properties, including fluid acquisition and reduced leakage, of absorbent articles while keeping the cost of production as low as possible. Furthermore, there is a need for articles that are easy to apply symmetrically on the wearer and conform to the shape of the body. The present invention addresses these multiple requirements.

SUMMARY OF THE INVENTION

The invention is directed to an absorbent core as well as an absorbent article comprising the absorbent core. The absorbent core comprises a core wrap having a top layer and a bottom layer enclosing an absorbent layer comprising superabsorbent polymer. The absorbent core is substantially free of cellulose fibers, and the absorbent layer comprises:
  a non-rectangular central portion having a front edge, a back edge and two longitudinally-extending side edges, wherein each side edge defines a recess along a portion of its length;
  a first side portion present in one of the recess and a second side portion present in the other recess, wherein each side portion comprises a proximal edge relative to the central portion and a distal edge further away from the central portion. The proximal edges of the side portions are convex. Furthermore either the distal edge of each side portion is concave so that the side portions are crescent-shaped; or the distal edge of each side portion is straight, and optionally flush with the longitudinally-extending side edge of the central layer outside the portion defining the recesses.

The absorbent core further comprises a first folding guide between the first side portion and the central portion, and a second folding guide between the second side portion and the central portion. The folding guides help the absorbent core to spontaneously form a three-dimensional basin when the absorbent core is folded into a basin-shaped tree-dimensional configuration, with the side portions forming side walls of the basin. The concave-shaped distal edges of the side portion can provide a better fit of the lateral edge of the article in which the absorbent core is incorporated, in particular as they may generally follow the curvature of the thighs of the wearer against which they abut. On the other hand, straight distal edges may also be used, as these may be easier to make and useful to provide a basin having higher sitting side edges, which may also be beneficial. The absorbent material of the absorbent core is substantially free of cellulose fibers, so that the absorbent core can be relatively thin and conformable, and thus more easily fold into the basin shape configuration when it is put in place on the wearer. The folding guides can be formed in various ways, but in particular by areas substantially free of absorbent material separating the central portion and the side portions.

The invention is also directed to an absorbent article comprising a wearer-facing side comprising a liquid-permeable topsheet, a garment-facing side comprising a liquid-impermeable backsheet and in-between an absorbent core as indicated above. The absorbent article can be notionally divided in a front region, a back region and an intermediate crotch region, each region measuring a third of the length of the article as measured along the longitudinal axis of the article. The central portion of the core can extend longitudinally across the front region, crotch region and back region of the article, and the side portions of the core are at least partially within the crotch region of the article. The absorbent article can further comprise elasticized elements, in particular a pair of elasticized leg cuffs and/or barrier leg cuffs. The elastic forces of the elasticized elements can help the article to spontaneously assume a bucket shape when the article is put on the wearer. The absorbent article can further comprise at least one liquid management layer between the topsheet and the absorbent core for efficiently acquiring and distributing fluid. The liquid management layer can optionally comprise folding guides generally superposed with the folding guides of the absorbent core.

BRIEF DESCRIPTION OF THE DRAWINGS

FIG. 2 is a transversal cross-section of the core of FIG. 1;
FIG. 3a is a schematic representation of the core of FIG. 1 in a folded state;
FIG. 3b is a schematic representation of the core of FIG. 1 in a folded state from another angle;
FIG. 4 is a transversal cross-section of the core of FIG. 1 in a folded state;
FIG. 6 is a transversal representation of a cross-section of the diaper of FIG. 5;
FIG. 7 is a transversal representation of a cross-section of an alternative diaper having folding guides in a liquid management layer superposed with the folding guides of the absorbent core;

FIG. 8 is a schematic representation of a cross-section of the article of FIG. 5 when worn between the thighs of a wearer;

FIG. 9 is a schematic representation of an alternative absorbent core according to the invention in a flat state.

DETAILED DESCRIPTION OF THE INVENTION

Introduction

As used herein in the specification and the claims, the term "central portion", "side portion" and "folding guide" without further qualification refer to these elements as part of the absorbent core, unless specified otherwise or wherein it is apparent from the context that these terms refer to another layer. When these terms are further qualified by "liquid management layer", as in "liquid management layer's central portion", they refer to these elements as part of the liquid management layer.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred, advantageous or exemplary embodiments described below are not limiting the scope of the claims, unless specifically indicated to do so. The words "typically", "normally", "preferably", "advantageously", "in particular" and the likes also qualify features which are not intended to limit the scope of the claims, unless specifically indicated to do so. Any feature or component described herein in relation with one embodiment may be combined with another feature or component of another embodiment unless indicated otherwise.

Figure 1:
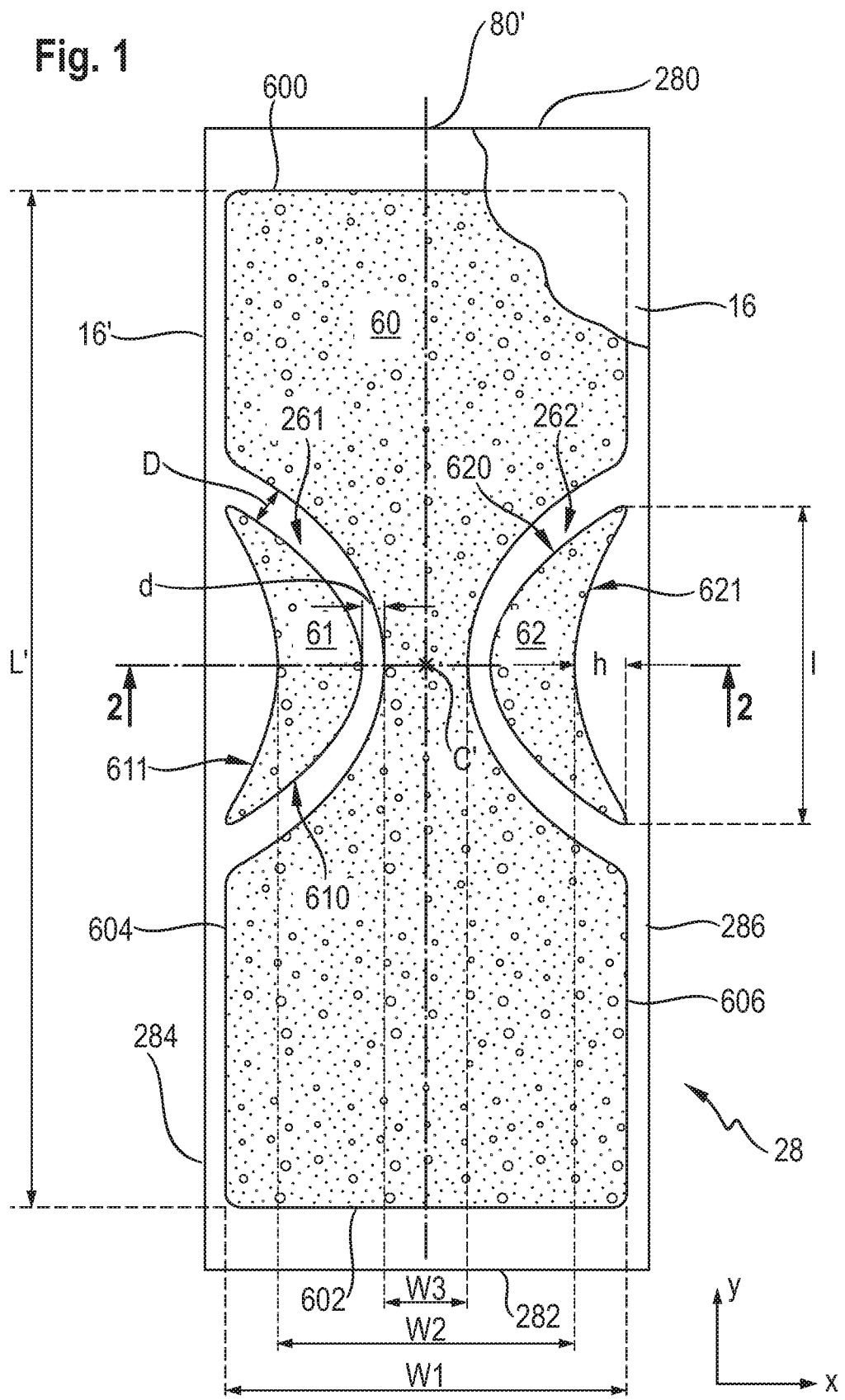
FIG. 1 is a schematic representation of an absorbent core according to the invention in a flat state.

Unless indicated otherwise, the description and claims refer to the absorbent article, absorbent core or component thereof before use (i.e. dry, and not loaded with a fluid) and conditioned at least 24 hours at 21° C.+/−2° C. and 50+/−20% Relative Humidity (RH) and in a flat state as shown for example on FIG. 1.

The absorbent articles of the invention and their components will now be discussed generally and with exemplary reference to the Figures and the numerals referred to in these Figures for illustration purpose. These examples are not intended to limit the scope of the claims unless specifically indicated.

General Description of the Absorbent Core 28

As used herein, the term "absorbent core" refers to a component of an absorbent article comprising an absorbent layer enclosed in a core wrap. The term "absorbent article" refers to a finished product that can be directly used by the user. The absorbent core can be typically an individual component which is attached directly or indirectly to other components of the articles such as a topsheet and a backsheet to form the article in a converting line. The core wrap is typically formed by one or two layers of nonwoven or tissue materials attached together, but it is not excluded that the absorbent core may be formed directly on the backsheet, the topsheet or another layer, in which case the core wrap may be at least partially formed by one of these layers. The absorbent core as used herein does not include a liquid management layer to acquire and distribute the fluid, which may be also typically present in an absorbent article. The absorbent core is typically the component of an absorbent article that has the most absorbent capacity of all the components of the absorbent article and which comprises all, or at least the majority of, superabsorbent polymer (SAP). The core may consist essentially of, or consist of, the core wrap, the absorbent material and optionally adhesives. The terms "absorbent core" and "core" are herein used interchangeably.

The absorbent cores of the invention are substantially planar. By substantially planar, it is meant that the absorbent core can be laid flat on a planar surface, as represented in FIG. 1. The absorbent cores may also be typically thin and conformable, so that they can also be laid on a curved surface for example a drum during the making process, or stored and handled as a continuous roll of stock material before being converted into an absorbent article. As represented in a flat state in FIG. 1, the absorbent core can be relatively thin relative to its other dimensions in the transversal direction (x) and the longitudinal direction (y). These directions correspond to the transversal and longitudinal direction of the article respectively. Unless otherwise indicated, dimensions and areas disclosed herein apply to the core in this flat-out configuration. The same applies to an absorbent article, as exemplarily represented in FIG. 4 as a taped diaper, in which the core may be integrated.

The absorbent cores and articles of the invention are now discussed with reference to the Figures and the numerals referred to in these Figures. These examples are not intended to limit the scope of the claims unless specifically indicated.

As illustrated in FIGS. 1 and 2, the absorbent cores 28 of the invention comprise a front edge 280, a back edge 282 and two longitudinal side edges 284, 286 joining the front edge and the back edge. The front edge of the core is the edge intended to be placed towards the front edge of the absorbent article in which the core is or will be integrated. Typically the front and back edges 280, 282 of the core may be shorter than the longitudinal side edges 284, 286 of the core. The absorbent core also comprises a top side 288 and a bottom side 290. The top side of the core is placed or intended to be placed towards the wearer-facing side (topsheet 24) of the article and the bottom side is the side placed or intended to be placed towards the garment-facing side (backsheet 25) in the finished article.

The absorbent core can be notionally divided by a longitudinal axis 80' parallel to the longitudinal direction y and extending from the front edge 280 to the back edge 282 and dividing the core in two substantially symmetrical halves relative to this axis, when viewing the core in the plane formed by the longitudinal and transversal direction (x, y). The absorbent core notionally has on its longitudinal axis 80' a crotch point C' which correspond vertically with the crotch point C of the absorbent core.

The core wrap may be formed by any substrate materials suitable for receiving and containing the absorbent material. Typical substrate materials used are in particular nonwovens, paper, tissues, films, wovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 and US2011/0250413A1. Nonwoven materials provided from synthetic fibers may be used, such as PE, PET and in particular PP.

The core wrap may, as shown in the cross-sectional view of FIG. 2, comprise a top layer 16 (also referred herein as first substrate) forming the top side 288 of the core and a bottom layer 16' (second substrate) forming the bottom side 290 of the core. The first substrate may be advantageously more hydrophilic than the second substrate, for example after treatment with a wetting agent. Alternatively, it is also known in the art to make a core wrap out of a single substrate, or to use the backsheet or topsheet as substrate to directly, partially or completely form the core wrap. When two substrates are used, they may also form a C-wrap seal along each longitudinal side edges 284, 286 of the core as is known in the art. The core wrap is not considered as absorbent material for the purpose of calculating the percentage of SAP in the absorbent core. Examples of core wrap construction are further detailed in WO2014/093310.

Absorbent Material Layer

The absorbent core comprises an absorbent material layer encompassed within the core wrap. The absorbent material layer comprises a central portion 60, and two shorter side portions 61, 62 disposed on opposite sides of the longitudinal axis 80'. Each side portion is separated from the central portion by a folding guide 261, 262. The absorbent material layer and the folding guides are typically substantially symmetrical relative to the longitudinal axis.

The central portion longitudinally extends from a front edge 600 adjacent to the front edge 280 of the core to an back edge 202 adjacent to the back edge 282 of the core. The central layer has a length L' measured along the longitudinal axis 80. The core wrap may be typically sealed along its periphery so that the absorbent material layer typically does not extend to the very edge of the core wrap. However it is also possible that there is no core wrap seal on one or more sides of the absorbent core, for example along the front edge and back edge of the core. The central portion may be unitary, as represented, but it is not excluded that it comprises sub-portions, for example separated by further transversally-orientated folding guides to provide more flexibility in the longitudinal direction.

The central portion is shaped so that it forms at least two recesses in an intermediate position on its side edges 604, 606 between its front edge and the back edge. The overall shape of the central portion may in particular be a dog-bone or hour-glass shape when seen from the top of the core as illustrated in FIG. 1. The width of the central portion has thus a minimum value W3 at an intermediate longitudinal position between the front edge and back edge of the central portion. The minimum width of the central portion may for example range from 10% to 70% of the maximum width, in particular from 20% to 60%, or from 30% to 50% of the maximum width W1 of the central portion. The central portion may have a constant width in the areas outside the recesses, but other configurations are possible, for example the width may continuously expand towards the front and/or back edges of the core.

Side Portions 61, 62

The side portions 61, 62 of the absorbent material layer are at least partially disposed in the recesses of the central portion 60. Each side portion comprises a proximal edge 610,620 closest to the central portion and an opposed distal edge 611, 621. The length l of the side portions as measured parallel to the longitudinal axis 80' is shorter than the length L' of the central portion, for example the length l may range from 10% to 80%, in particular from 20% to 70%, or from 30% to 60% of the length of the central portion of the absorbent layer.

In a first aspect of the invention, the proximal edge and the distal edge may be both concave towards the central portion, as illustrated in FIG. 1, so that these proximal edges form a bulge towards the longitudinal axis. The inner and distal edges may in particular be curved, as illustrated in FIG. 1, but it is not excluded that one or both of the edges are at least partially formed by converging straight lines, for example having a flattened V shape. The side portions may be each defined entirely by their proximal edge and their distal edge, and may thus be generally crescent-shaped. Distal edges which are generally concave can provide a better fit of the lateral edges of the article in which the absorbent core is incorporated. The concave distal edges may in particular generally follow the curvature of the thighs of the wearer against which they abut. The maximum height h of the concave distal edge as measured parallel to the transversal direction between its point closest to the longitudinal side edge of the core and its point closest to the longitudinal axis of the core may for example represent from 5% to 20% of the maximum width W1 of the central portion. The distance W2 between the two closest points of both distal edges 611, 621 of the side portions may for example range from 50% to 90% of the maximum width W3. This improved fit combined with the basin shape taken by the absorbent core when it is worn provide for improved comfort of the article in which the core is integrated.

In a second aspect of the invention, as illustrated in FIG. 9, the absorbent core of the invention may comprise side portions each having a distal edge 611, 621 which is straight and oriented longitudinally rather than concave as previously discussed in relation to FIG. 1. The distal edge 611 of the core may be in particular flush with the side edges of the central layer outside the portion of the longitudinal edge defining the recesses as represented. Such straight distal edges may also be placed further within the recesses than illustrated and thus not extend to the edge of the longitudinal side edges of the central layer. While having straight distal edges may be less advantageous in terms of dry and wet fit of the article along the thighs of the users, they may be easier to manufacture and can provide higher side portions for the absorbent core in the basin-shaped configuration.

Folding Guides 261, 262

The central portion 60 and the first side portion 61 are separated by a first folding guide 261, and likewise the central portion 60 and the second side portion 62 are separated by a second folding guide 262. The folding guides facilitate the folding of the absorbent core so that the core forms a three-dimensional shape similar to a basin, as illustrated in FIG. 3A-3B, when the article in which it is incorporated is placed on a wearer. The side portions of the absorbent material layer form the side walls of the basin, while the front and back sides of the central portion are tilted upwards towards each other. The folding guides may in particular be areas substantially free of absorbent material between the central portion and the side portions. By "substantially free" it is meant that accidental contamination by some absorbent material such as SAP particles during the making process is not excluded. In this case, the width of absorbent material-free areas may be substantially constant through the folding guides or may vary, for example the width of the material-free areas may gradually increase from a minimum (d) towards the middle of the folding guide to a maximum (D) towards one or both extremities of each of the folding guides. As represented in FIG. 2, the top layer 16 of the core wrap may be advantageously bonded to the bottom layer 16' through the folding guides. This bond 70 may be for example an adhesive bond, a mechanical bond, a fusion bond, an ultrasonic bond or any combinations of these, formed through the folding guides. The core wrap may also be bonded in other areas of the core, for example in the areas 71 outward of the distal edges of the side portions, and also to form the C-wrap seals 72 along the longitudinally-extending side edges of the core, as shown on FIG. 2.

The folding guides may advantageously be curved towards the central portion 60, and the recesses of the central portion, the proximal side edges of the side portions and the folding guides may generally run parallel to each other. In particular, both extremities of each folding guides may completely extend to the longitudinally-extending side edges of the absorbent layer, as illustrated in FIG. 1, thus completely separating the side portions and the central portion, when the article and core are considered in a flattened out configuration. In other words, the folding guides are advantageously not completely surrounded by absorbent material. In this way, the side portions can easily fold relative to the central portion to provide the upstanding side walls of the basin in the folded basin configuration. The folding guides may be curved along a smooth curve without inflexion points, as in a couple of inverted brackets: ) (. It is also possible that each of the folding guides may form a curve or a series of segments having an inflexion point at their closest position from each other, for example each being generally "v" shaped with a 90° rotation, thus appearing together as a pair of sign bigger than and smaller than: > <.

The folding guides may be continuous along their entire length as illustrated in FIGS. 1 and 9, but it is not excluded that the folding guides are intermittently formed, for example by a series of discrete material free areas or embossed areas each separated by small gaps, as long as the discrete sections are sufficiently close and aligned to provide for the desired folding guide function.

The folding guides may be more generally provided by any means known in the art, for example as disclosed in WO2006/068549A1 (Hansson) and have any shape, in particular be straight and parallel to the longitudinal direction 80. The folding guides may be for example grooves or channels having a certain width, for example from 1 mm to 20 mm, and comprising either no absorbent material or some absorbent material at a lower basis weight than the surrounding areas of the absorbent layer, for example having a basis weight which is from 10% to 80%, in particular 15% to 70%, of the basis weight of the immediately adjacent central portion and/or side portions. A folding guide may be also provided by embossing an absorbent material which is permanently compressible such as a fibrous absorbent material or foam. In this case, the folding guides may be formed by grooves having a higher degree of compression than the surrounding areas of the absorbent layer. It is also known to form folding guides by slitting the material of an absorbent layer, if the absorbent material can be slit such as some solid foam-like absorbent material. Of course a combination of these means can be used to form the folding guides. The folding guides have a centerline generally following the guides along their middle.

Absorbent Material

The absorbent core comprises an absorbent material which is substantially free of cellulose fibers. The absorbent material may be the same in the central portion 60 and the side portions 61, 62, for simplicity of manufacture, but it is not excluded that different materials are used in the central portion and the side portions for example. The absorbent material may typically comprise a high proportion of superabsorbent polymer (herein abbreviated as "SAP"). The term "superabsorbent polymer" refers herein to absorbent materials, which may be cross-linked polymeric materials, and that can absorb at least 15 times their weight of an aqueous 0.9% saline solution as measured using the Centrifuge Retention Capacity (CRC) test (EDANA method WSP 241.2-05E). The SAP may in particular have a CRC value of from 20 to 50 g/g, or from 25 to 40 g/g. The SAP may in particular be in particulate forms (SAP particles) but other forms are also possible, such as absorbent foam or fibers. Further detailed examples of absorbent material, in particular SAP, are disclosed in WO2014/093310 (Ehrnsperger). The absorbent material may also comprise or consist of SAP particles that require a time to reach an uptake of 20 g/g (T20) of less than 240s as measured according to the K(t) test method described in WO2012/174026 (Ehrnsperger). The SAP particles used may have a permeability at equilibrium expressed as UPM (Urine Permeability Measurement) value of at least $10 \times 10^{-7}$ $(cm^3 \cdot s)/g$, in particular at least $15 \times 10^{-7}$ $(cm^3 \cdot s)/g$, or at least $20 \times 10^{-7}$ $(cm^3 \cdot s)/g$, or from 10 to $50 \times 10^{-7}$ $(cm^3 \cdot s)/g$, as measured by the test method indicated in WO2012/174026A1.

The absorbent core is substantially free of cellulose fibers, comprising less than 15% by weight of cellulose fibers relative to the total weight of absorbent material, in particular less than 10%, or less than 5% and down to 0% by weight of cellulose fibers. The absorbent core may thus be relatively thin, in particular thinner than conventional cores comprising cellulosic fibers. In particular, the caliper of the core (before use) as measured at the point corresponding to the crotch point C of the article, or advantageously at any points of the surface of the core, may be from 0.25 mm to 5.0 mm, in particular from 0.5 mm to 4.0 mm, as measured according to the Thickness Measurement Method described further below.

Figure 5:
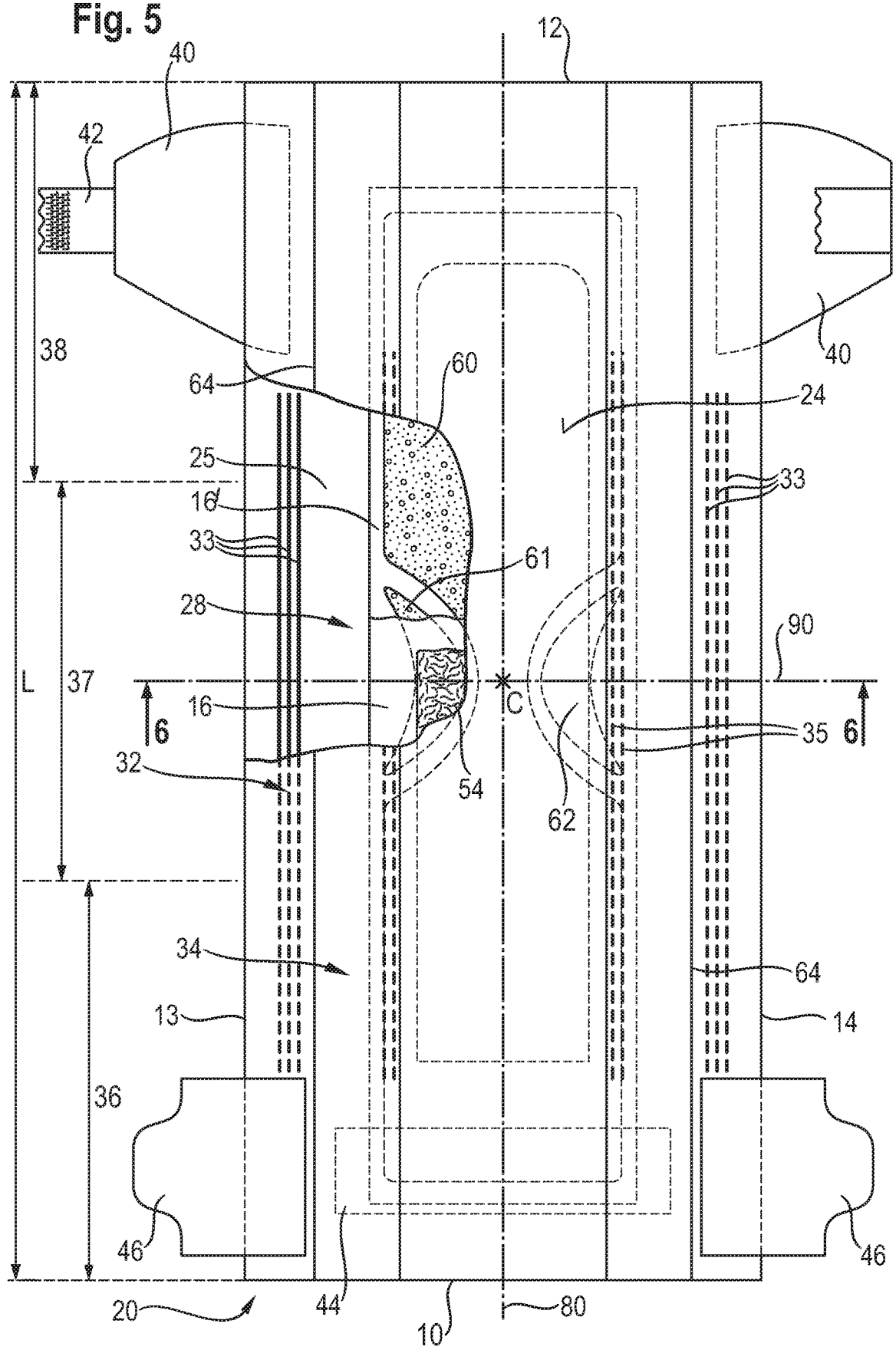
FIG. 5 is a top view of an exemplary absorbent article in the form of a taped diaper, flattened-out, and with some layers partially removed to better show the inner layers.

The absorbent material layer may be continuous in the central portion and the side portions, as exemplary illustrated in FIG. 5. A continuous layer of absorbent material may in particular be obtained by the addition of two discontinuous absorbent sub-layers as taught in US2008/312617 (Hundorf), the first absorbent sub-layer including a first substrate and the second absorbent sub-layer including a second substrate, the first and second absorbent sub-layers further including superabsorbent particulate polymer material deposited on said first and second substrates and thermoplastic adhesive material covering the absorbent particulate polymer material on the respective first and second substrates. The first and second absorbent sub-layers are combined together such that at least a portion of said thermoplastic adhesive material of said first absorbent sub-layer contacts at least a portion of the thermoplastic adhesive material of the second sub-absorbent layer, the resulting absorbent particulate polymer material layer between the first and second substrates may be thus substantially continuously distributed across the absorbent particulate polymer material area. It is also not excluded that the central and side portions may comprise a multiplicity of land areas comprising the absorbent material, with absorbent material-free junction areas in-between, as is known in the art for example in US2008/312625 (Hundorf).

The basis weight (amount deposited per unit of surface) of the absorbent material may also be varied to create a macroscopically profiled distribution of absorbent material in the longitudinal direction and/or the transversal direction. Typically the absorbent material of the core may be advantageously distributed in somewhat lower amount towards the back edge of the core as more absorbency is typically required towards the front and middle region of the core. Further detailed examples of absorbent material distribution that can be used herein are disclosed in WO2014/093310 (Ehrnsperger). The side portions may comprise an absorbent material at a constant basis weight or may also have a profiled distribution. The central portion may typically comprise a larger overall amount of absorbent material than the two side portions combined, for example in a ratio ranging from 20:1 to 2:1.

The absorbent material may be deposited on a substrate to form the central portion and the side portions by adapting any known processes that allow relatively precise deposition of absorbent material, in particular SAP, advantageously at relatively high speed. The absorbent material may be deposited for example using a SAP printing technology as disclosed in US2006/024433 (Blessing), US2008/0312617 and US2010/0051166A1 (both to Hundorf et al.). This technique uses a transfer device such as a printing roll to deposit SAP particles onto a substrate disposed on the grid of a support (e.g. a lay-on drum). The grid may include a plurality of cross bars extending substantially parallel to and spaced from one another so as to form ribs extending between the cross-bars. The SAP is deposited in the undulations of the substrate inside these ribs. As known in the art indicated above, two such SAP printing roll/laying-on drum systems working in parallel can be used to print twice a SAP layer on two substrates, the substrates being then assembled with the SAP layers in contact with each other thus forming a continuous layer of SAP between a top layer and a bottom layer (the core wrap). This technology allows high-speed and precise deposition of SAP on a substrate in a desired pattern.

US2012/0312491 (Jackels) more recently discloses how raised elements on the transfer device may collaborate with corresponding mating strips on the support grid to provide areas free of deposited absorbent material. The printing roll and the lay-on drum are further adapted to provide the desired SAP application pattern, in particular shaping the central and side portions as desired. The top and bottom layers of the core wrap can be bonded together through some of these material-free areas to form the folding guides and the gaps between the winglets. Thus a SAP printing technique may be advantageously used to make absorbent cores according to the invention. Of course it is not excluded that other manufacturing techniques may be used, or that products are hand-made for research purpose for example.

Further Components of the Absorbent Core

The absorbent core may comprise one or more layers of glue to help immobilizing the absorbent material, for example as disclosed in US2006/024433 (Blessing), US2008/0312627 and US2010/051166A1 (both to Hundorf et al.) and US2014/027066A1 (Jackels).

The absorbent core may in particular comprise at least one auxiliary glue layer applied on the inner surface of the top side and/or the bottom side of the core wrap. The auxiliary glue may be applied directly over the substrate on which the absorbent material is subsequently deposited, thus at least partially immobilizing the absorbent material on the substrate. The auxiliary glue may also at least partially form a core wrap bond within the folding guide areas. The auxiliary glue may also be useful to improve the adhesion of a fibrous thermoplastic material, when present, to the substrate. The auxiliary glue can be applied by any adhesive applicator known in the field, in particular bead, slot or spray nozzles. For example, the auxiliary glue can be applied using a slot coating process as a pattern comprising a plurality of spaced-apart slots which may each extend in the longitudinal direction. The slots may for example have a width of from 0.5 mm to 3 mm, and/or have a lateral spacing there-between of from 0.5 mm to 4 mm. The auxiliary glue may be applied along the whole length of absorbent core or intermittently along a shorter length, for example at least in the area of the folding guides.

The absorbent core may also comprise a fibrous thermoplastic adhesive material (not shown), also known as microfibrous glue, to help immobilizing the absorbent material within the core wrap. The fibrous thermoplastic adhesive material may be applied, typically by spraying, over an absorbent material that has been discontinuously deposited on a substrate during the core making process, thus forming land and junction areas as indicated above. The fibrous thermoplastic adhesive material contacts the absorbent material and the substrate layer in the absorbent material free junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material, and thereby immobilizes this absorbent material. A dual layer core can thus be constructed wherein the land areas of one layer correspond to the material-free junction areas of the other layer and vice versa, resulting in continuous dual absorbent layer.

The adhesive material may advantageously help providing a high immobilization of the absorbent material in dry and wet state. The absorbent core advantageously achieve an SAP loss of no more than about 70%, 60%, 50%, 40%, 30%, 20%, or 10% according to the Wet Immobilization Test described in US2010/051166A1.

Absorbent Article

The absorbent cores of the invention may be used in any absorbent articles of the type used by an incontinent individual to absorb body exudates such a urine. The term absorbent articles as used herein include in particular baby and toddler diapers (including training pants), feminine sanitary pads and adult incontinence articles.

An exemplary absorbent article according to the invention is represented in FIG. 5 in the form of a taped diaper 20. FIG. 5 is a top plan view of the exemplary diaper 20, in a flat-out state, with portions of the structure being cut-away to more clearly show the construction of the diaper. This diaper 20 is shown for illustration purpose only. The absorbent article can also be for example a pant-type article with pre-formed side seams. Unless otherwise indicated, dimensions and areas disclosed herein apply to the article in this flat-out configuration. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface.

The absorbent article 20 comprises a front edge 10, a back edge 12, and two longitudinally-extending side (lateral) edges 13, 14 joining the front edge and the back edge. The front edge 10 is the edge of the article which is intended to be placed towards the front of the user when worn, and the back edge 12 is the opposite edge. The absorbent article is notionally divided by a longitudinal axis 80 extending from the front edge to the back edge of the article and dividing the article in two substantially symmetrical halves relative to this axis, when viewing the article from the wearer facing side in a flat out configuration, as exemplarily shown in FIG. 5. This axis 80 may typically be concomitant with the longitudinal axis 80' of the absorbent core. The article has a length L as measured along the axis 80 from the back edge to the front edge. The absorbent article 20 can also be notionally divided by a transversal axis 90 into a front region and a back region of equal length measured on the longitudinal axis, when the article is in such a flat state. This article's transversal axis 90 is perpendicular to the longitudinal axis 80 and placed at half the length of the article. The intersection of the longitudinal axis and transversal axis are referred herein as the Crotch Point "C".

The absorbent article is further notionally divided in a front region, 36, a back region 38 and a crotch region 37 in between. The front region 36 is defined as the region of the article extending from the front edge 10 and having a length of a third of L along the longitudinal axis 80. The back region 38 is defined as the region of article extending from the back edge 12 of the article and having a length of one third of L along the longitudinal axis 80. The crotch region 37 is the intermediate region between the front and back regions, and also having a length of a third of L along the longitudinal axis 80.

The absorbent article 20 comprises a wearer-facing side, which may be principally formed by a liquid permeable topsheet 24, a garment-facing surface which may be formed by a liquid impermeable backsheet 25, and an absorbent core 28 between the topsheet 24 and the backsheet 25. The absorbent core 28 is shown in isolation in FIG. 1 but of course any absorbent cores according to the invention may be used, for example as shown in FIG. 9. The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. Nos. 3,860,003, 5,221,274, 5,554,145, 5,569,234, 5,580,411, and 6,004,306. The absorbent article is preferably thin, for example with a caliper of from 2.0 mm to 8.0 mm, in particular from 3.0 mm to 6.0 mm, a the crotch point as measured using the Thickness Measurement Method described below.

Liquid Management Layer(s) 54

The absorbent articles may advantageously comprise at least one liquid management layer 54 at least partially present between the topsheet and the absorbent core. Liquid management layers function to quickly acquire and/or distribute the fluid away from the topsheet and into the core. These liquid management layers are sometimes called "wicking layer", "surge layer", "acquisition layer" or "distribution layer". Typically, liquid management layers do not comprise SAP, as this may slow the acquisition and distribution of the fluid. The prior art discloses many type of liquid management layer, see for example WO2000/59430 (Daley), WO95/10996 (Richards), U.S. Pat. No. 5,700,254 (McDowall), WO02/067809 (Graef). Liquid management layers are typically placed symmetrically relative to the longitudinal axis of the article, but other configurations are possible. The liquid management layers may be typically shorter at least in the longitudinal dimension and typically also in the transversal direction relative to the absorbent material layer of the absorbent core.

Liquid management layers help improving the fluid handling properties of the article, in particular for those articles having no or relatively little cellulose fibers in the absorbent core. Cellulose fibers can typically help acquiring and distributing the fluid within the core. In the present invention, where the absorbent material of the core is substantially free of cellulose fibers, it is thus advantageous to have at least one liquid management layer.

Advantageously, the liquid management layer should not hinder or provide a significant resistance to the folding of the core and article in the desired basin shape. The liquid management layer may thus be sufficiently conformable and flexible for this purpose as illustrated in FIG. 8, for example the layer may comprise unbound or loosely bound hydrophilic fibers. In this case, there is no specific restriction as to the shape and placement of the liquid management layer. As illustrated in FIGS. 5-6 the liquid management layer may then be rectangular and overlap with the folding guides of the absorbent core. It also possible to provide a liquid management layer which is shaped or rectangular, having a width that does not extend transversally outward of the central portion of the absorbent core.

It is also possible to provide the liquid management layer with folding guides 261', 262' which are at least partially generally superposed with the folding guides of the absorbent core, as illustrated in FIG. 7. Thus the liquid management layer can easily fold in a similar manner than the core when it forms the three-dimensional basin. The liquid management layer may thus comprise a central portion, (also referred herein as "liquid management layer's central portion"), a first and a second side portions (also referred herein as "liquid management layer's first and second side portions"), and a first and a second folding guides (referred herein as "liquid management layer's folding guides") between the liquid management layer's central portion and the first and second liquid management layer's side portions respectively. By "generally superposed", it is meant that the position and shape of the folding guides of the liquid management layer vertically correspond to the underlying folding guides of the absorbent core, so that the liquid management layer can readily assume the shape of the basin formed by the underlying absorbent core when the article is put on and worn by the wearer.

It is not necessary that the folding guides of the two layers are exactly superposed, and there may be for example a slight transversal shift due to the unavoidable process tolerance in modern high speed making process or to take into account the thickness of the layers when forming the three-dimensional basin. Thus it may be acceptable that the center lines of both folding guides are within a distance of 10 mm or less, for example 5 mm, from each other when considered in the plane of the article. The liquid management layer's folding guides may be superposed with the folding guides of the absorbent core over the whole length of the liquid management layer's folding guides, but a lower percentage of overlap is also possible. It is not excluded that there may be areas where the folding guides of these layers do not overlap, or the folding guides of one layer may be shorter than the folding guides of another layer. For example, the liquid management layer's folding guides may overlap over at least 50%, 60%, 70% or more of the overall length of the absorbent core's folding guides. In the remaining areas where there is no overlap, the liquid management layer's folding guides may for example be off-set relative to the absorbent core's folding guides, or may be shorter and thus not extend to the same length as the absorbent's core folding guides.

The article of the invention may also comprise two or more liquid management layers, and these may form a unitary layer or remain discrete layers, which may be loosely attached to each other. The article may in particular comprise two liquid management layers: an acquisition layer directly under the topsheet and a distribution layer between the acquisition layer and the absorbent core. Such dual layer liquid management layers are for example disclosed in further details in WO2014/093323 (Bianchi) with a distribution layer comprising cross-linked cellulosic fibers and the acquisition layer a carded, resin-bonded nonwoven. The invention is however not restricted to this example having two liquid management layers. The majority of articles have in particular for cost reason only one liquid management layer. As indicated previously, there may also be no liquid management layer between the absorbent core and the topsheet, and/or one such layer may be present under the absorbent core, between the absorbent core and the backsheet. The following will describe in more details two examples of liquid management layers, which may be respectively used as an acquisition layer and a distribution layer alone in an article or in combination.

The function of a distribution layer is to spread the insulting fluid liquid over a larger surface within the article so that the absorbent capacity of the core can be more efficiently used. Typically, distribution layers can be made of a material comprising synthetic or cellulosic fibers and having a relatively low density. The distribution layer material may be a nonwoven or a fibrous layer comprising unbound or loosely bound hydrophilic fibers, in particular a layer of cross-linked cellulosic fibers. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer may also be a material having a water retention value of from 25 to 60, preferably from 30 to 45, measured as indicated in the procedure disclosed in U.S. Pat. No. 5,137,537.

Such a liquid management layer 54 may for example comprise at least 50% by weight, optionally consisting of 100%, of cross-linked cellulosic fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf), however not in the manner of the invention. The cross-linked cellulosic fibers provide higher resilience and therefore higher resistance against the compression in the product packaging or in use conditions, e.g. under baby weight. This provides the layer with a higher void volume, permeability and liquid absorption, and hence reduced leakage and improved dryness. The liquid management layer 54 may also be typically profiled so that more material is present at the front and middle part of the article relative to the back of the article. The distribution layer may typically have an average basis weight of from 30 to 400 g/m$^2$, in particular from 100 to 300 g/m$^2$, with the basis weight varying along the length of the article so that more material is present at the front and middle of the layer than at the back. The liquid management layer may thus be profiled and/or shaped rounded towards the back of the article, as exemplarily disclosed in WO2014/093323 (Bianchi).

If folding guides 261', 262' are present in such a distribution layer, they may be formed by areas substantially free of the liquid management material, in this case substantially free of unbound or loosely bound hydrophilic fibers such as cross-linked cellulosic fibers as illustrated in FIG. 7. Such a fibrous distribution layer may for example be made on-line by depositing the fibers, for example cross-lined cellulosic fibers, on a forming surface having ridges corresponding to the areas where no fibrous material is desired. Deposition chambers are known wherein a carrier sheet is provided on a forming surface having a series of holes connected to a vacuum, so that the vacuum pulls the fibers in the desired emplacements to form a desired deposited layer. The forming surface of these deposition chambers can be modified to provide a layer of fibrous material having a central portion, side portions separated by folding guides and optionally winglets. The fibrous layer is typically formed or transferred on a carrier sheet that should thus have at least the same dimension as a fibrous liquid management layer. The carrier sheet may be the topsheet, another liquid management layer such as a nonwoven acquisition layer, or any other layer of the article, for example the core wrap.

Another type of liquid management layer that may be used for example as an acquisition layer, may be made of a nonwoven web rather than loosely bound fibers as for the distribution layer discussed before. The nonwoven web may be for example provided as a continuous roll of material that is cut according to the desired length and pattern as it unwound in a converting line. A "nonwoven web" or "nonwoven" as used herein means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m$^2$ or gsm).

Such an acquisition layer is typically placed directly under the topsheet, and above a distribution layer if such a layer is present. The acquisition layer may typically be or comprise a nonwoven, for example a through-air bonded ("TAB") carded nonwoven, a resin-bonded ("RB") carded nonwoven, a spunbond or spunlace (hydroentangled) nonwoven. TAB carded nonwovens may for example be made from soft PE/PP bicomponent staple fibers. The air through bonding process locks in loft and compressibility. Resin-bonded carded nonwovens may be made from multi-denier polyester staple fibers (for example: 50/50 or 40/60 mix of 6 denier and 9 denier fibers). Its resilient and open structures are designed to provide excellent fluid acquisition properties. Such acquisition layers are available directly from suppliers, e.g. Fitesa of Simpsonville, S.C., USA or TWE Group GmbH, of Emsdetten, Germany. The nonwoven layer may be stabilized by a latex binder for example a styrene-butadiene latex binder (SB latex). Processes for obtaining such latexes are known, for example from EP149,880 (Kwok), US2002/028858 and US2003/0105190 (Diehl). The binder may typically be present in an acquisition layer in excess of about 12%, about 14% or about 16% by weight of the layer. A SB latex is for example commercially available under the trade name GENFLO™ 3160 (OM-NOVA Solutions Inc.; Akron, Ohio). Latex bonded acquisition layers are for example further disclosed in US2005/033252A1, US2005/033253A1 or US2005/043694A1

(Schneider). The basis weight of acquisition layers may typically range from 10 gsm to 200 gsm, in particular 20 gsm to 140 gsm, or 40 gsm to 120 gsm, for example 80 gsm.

Such a nonwoven liquid management layer may also optionally comprise folding guides at least partially generally superposed with the folding guides of the absorbent article, and thus delimiting a central portion and side portions. For a liquid management layer formed from a nonwoven material, it may be more practical to form the liquid management layer folding guides by compressing or slitting the nonwoven material according to desired pattern rather than providing material free areas. These cuttings or slitting operations may be made online using conventional tools such as slitting tools, embossing tools or cutting tools.

A further acquisition layer (not represented) may be used in addition to a first acquisition layer described above. For example a tissue layer may be placed between an acquisition layer and a distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

Topsheet 24

The topsheet may be made according to any topsheet known in the art for absorbent articles. The topsheet is preferably compliant, soft-feeling, and non-irritating to the wearer's skin. Further, at least a portion of the topsheet is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8. Typical diaper topsheets have a basis weight of from about 10 to about 28 gsm, in particular between from about 12 to about 18 gsm but other basis weights are possible.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T".

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839, (Cramer et al.) and U.S. Pat. No. 7,112,621 (Rohrbaugh et al). Any portion of the topsheet may also be coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Although not shown in the drawings, it is possible to bond the topsheet directly or indirectly to the folding guides of the absorbent core. If a liquid management layer is present between the topsheet and the backsheet, the topsheet may also be bonded to or through the folding guide of the liquid management layer. The topsheet may be bonded by any known bonding means, typically adhesive bonding, pressure bonding or heat bonding, or a combination of these. Similarly the topsheet may also be directly or indirectly bonded to at least some of the areas of the core wrap corresponding to the gaps between the winglets of the absorbent core.

Backsheet 25

The backsheet 25 may also be made according to any backsheet known in the art for absorbent articles. The backsheet 25 is typically impermeable to liquids (e.g. urine) so that it keeps the garment-facing side of the article dry. The backsheet may for example be or comprise a thin plastic film such as a thermoplastic film having a thickness of less than about 0.10 mm. Exemplary backsheet films include those manufactured by Tredegar Corporation, based in Richmond, Va., and sold under the trade name CPC2 film. Other suitable backsheet materials may include breathable materials which permit vapors to escape from the article while still preventing exudates from passing through the backsheet. A covering low basis weight nonwoven may be attached to the external surface of the film to provide for a softer touch.

Other Components of the Article

The absorbent articles of the invention can comprise any typical components known for the intended purpose of the article. FIGS. 5-6 show other typical taped diaper components not further discussed herein such as a fastening system comprising fastening tabs 42 attached towards the back edge 12 of the article and cooperating with a landing zone 44 placed towards the front edge 10 of the article. These fastening features are typically absent from pant-type articles which have a pre-formed side seam, nevertheless the invention may of course also be used in such pant-types articles. The absorbent article may also comprise other typical components, which are not represented in the Figures, such as a back elastic waist feature, a front elastic waist feature, transverse barrier element across the topsheet, a wetness indicator between the core and the backsheet that changes appearance when contacted with urine, a lotion application on the topsheet, etc. These components are well-known in the art and will not be further discussed herein. Reference is made to WO2014/093310 where several examples of these components are disclosed in more details.

The absorbent articles may typically further comprise components that improve the fit of the article around the legs of the wearer, in particular a pair of barrier leg cuffs 34 and gasketing cuffs 32. The barrier leg cuffs 34 may each be formed by a piece of material, typically a nonwoven, that can be partially raised away and thus stand up from the plane defined by the topsheet, as shown for example in FIGS. 6-7. The barrier leg cuffs thus comprise a first portion 64 flush with the topsheet and limited inwardly by a proximal edge 65. This first portion may be attached to the topsheet and/or backsheet with an intermittent or continuous fusion bond and/or a glue bond. The barrier leg cuffs 34 further comprise a free-standing portion limited by a distal edge 66, which in use fits at the junction of the thighs with the torso of the wearer, at least in the crotch region 37 of the article. The barrier leg cuffs can provide improved containment of liquids and other body exudates approximately at the junction of the torso and legs of the wearer. Typically, the barrier leg cuffs are formed from a separate material joined to the rest of the article, in particular to the topsheet, but it is not excluded that the barrier leg cuffs can be integral with (i.e. formed from) the topsheet or the backsheet, or any other layer, for example the bottom layer of the core wrap. Typically the material of the barrier leg cuffs may extend through the whole length of the article but is further bonded to the topsheet towards the front edge and back edge of the article so that in these sections the barrier leg cuff material remains flush with the topsheet (tack bonds not shown in FIG. 5 for readability). Each barrier leg cuff 34 typically comprises one, two or more elastic strings 35 close to this free standing terminal edge 66.

The contractive elastic forces provided at the distal end 66 of the barrier leg cuffs can help folding the absorbent core and thus the absorbent article into a basin shape. Thus the elastic strings 35 will not only cause the barrier leg cuffs to stand up, but they will advantageously also pull the side portions 61, 62 of the absorbent core upwards, with these side portions hinging on the folding guides 261,262. When present, the corresponding side portions of a liquid management layer 54 will also stand up to form absorbent side walls.

In addition to the barrier leg cuffs 34, the article may typically comprise gasketing cuffs 32, which may be present as part of the chassis of the absorbent article. The gasketing cuffs may be at least partially enclosed between the topsheet and the backsheet, or the barrier leg cuffs and the backsheet. The gasketing cuffs may be placed transversally outward relative to the proximal edge 65 of the barrier leg cuffs 34. The gasketing cuffs 32 can provide a better seal around the thighs of the wearer. Usually each gasketing cuff 32 will comprise one or more elastic string or elastic element(s) 33 embedded within the chassis of the diaper, for example between the topsheet and backsheet in the area of the leg openings. These elastic elements 33 may, independently or in combination with the elastics 35 of the barrier leg cuffs, help shaping the absorbent article into a basin shape when put in place and being worn by the user.

Various cuff constructions have been disclosed for in the art and may be used in the present invention. U.S. Pat. No. 3,860,003 describes a disposable diaper which provides a contractible leg opening having a side flap and one or more elastic members to provide gasketing cuffs. U.S. Pat. Nos. 4,808,178 and 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. More recently, WO2005/105010 (Ashton) discloses a dual cuff system made of a continuous cuff material. All or a portion of the barrier leg and/or gasketing cuffs may be treated with a lotion.

Although not represented, the article of the invention may further comprise other longitudinally-extending elasticized elements as known in the prior art, in particular elements which may be at least partially placed between the side portions 61, 62 of the absorbent layer and the backsheet, and whose function is to further help folding the article along the folding lines when it is put in place and worn by the user. For example WO2006/068549 (Hansson) discloses having at least two stretchable crotch elastic members in the crotch portion and attached to the absorbent core and/or one of the topsheet or backsheet, wherein at least a substantial portion of the crotch elastic members are positioned laterally outside the respective folding guides. WO95/16418 (Wildlund) discloses having two elastic threads fastened in a stretched state to the topsheet and extending from the front of the article to the back of the article. The threads are mutually convergent.

The combined elastic forces provided by the different elasticized components of the article may thus bring or facilitate bringing the article into a basin shape when the article is placed on a wearer.

More generally, adjacent layers within the article will be joined together using conventional bonding method such as adhesive coating via slot coating, spiral gluing, or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers. For example, the backsheet and the core wrap may be glued using a core-to-backsheet gluing pattern as disclosed in WO2012/170341A1 (Hippe), or a full coverage pattern using several spiral glue applicators. If for example the backsheet is attached by gluing or otherwise to the areas of the core wrap corresponding to the folding guides (not shown), the folding guides may become more visible to the user from the garment-facing side of the article. Any typical hotmelt adhesives may be used. It is also possible to use a printed adhesive layer, for example between the topsheet and absorbent core or liquid management layer, which may be optionally visible through the topsheet, as exemplary disclosed in WO2014/078247.

Typically, adjacent layers will be joined together using conventional bonding method such as adhesive coating via slot coating, spiral gluing, or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap a disclosed in WO2012/170341A1. The adhesives used may be any standard hotmelt glue as known in the art.

Example

The following illustrates dimensions and material for an exemplary core similar to the one represented in FIG. 1. The absolute dimensions of the absorbent cores will vary with the intended uses. Absorbent cores for larger size diapers will typically be larger than absorbent cores for smaller sized diapers. The following are exemplary values for a core suitable for example in a "size 4" or "Midi" diaper, which can be indicated for baby weighing between 7 kg and 18 kg.

L'=360 mm
D=27 mm
d=3 mm
h=25 mm
l=93 mm
W1=110 mm
W2=61 mm
W3=23 mm

In this example, the core wrap comprises a top layer C-wrapped around a bottom layer and attached to it by gluing. The top layer has a width of 165 mm, the bottom layer has a width of 130 mm. The final core bag width is approximately 120 mm. The top layer can for example be a 10 gsm water permeable propylene spun bonded nonwoven (from Fitesa Germany), the bottom layer an hydrophobic 10 gsm nonwoven (from Fibertex). The core wrap may also be sandwiched sealed by fusion bond or gluing at its font end and its back end.

The absorbent material can for example consist entirely of SAP particles, in this case CA L700, ex Nippon Shok. Group immobilized by a microfibrous glue and optionally an auxiliary slot glue layer on one side of the core wrap.

The total amount of SAP may be 12.7 g. The SAP is advantageously profiled so that more absorbency is available towards the middle and the front of the core. Hand-made cores were made using a pattern comprising seven sections ("septile") distributed in the longitudinal direction. Within a septile, the SAP was evenly distributed. The first septile is the closest to the front edge 280 of the core and the last septile closest to the back edge of the core.

| Septile No. | Length [mm] | Cumulative Length [mm] | AGM amount [g] |
|---|---|---|---|
| 1 | 54.75 | 54.75 | 2.02 |
| 2 | 54.75 | 109.5 | 2.36 |
| 3 | 54.75 | 164.25 | 2.85 |
| 4 | 54.75 | 219 | 2.58 |
| 5 | 54.75 | 273.75 | 1.65 |
| 6 | 54.75 | 328.5 | 0.87 |
| 7 | 31.5 | 360 | 0.38 |

The total length of the core wrap was about 10 mm longer in the front and in the back than the central absorbent material portion to provide for a sandwich front and end core wrap seal.

Packaging

The absorbent articles may be packaged in any type of conventional packaging. The absorbent articles may be in particular compressed when packaged to save space. The package may thus comprise a plurality of bi-folded absorbent articles, wherein the articles in the package have an in-bag stack height of less than about 80 mm, according to the In-Bag Stack Height Test as described in WO2011/041352 (Weisman et al.), incorporated herein by reference.

The packaged absorbent articles may for example have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test.

Many absorbent articles are bi-folded along their transversal centerline 90 when packed in their bags. When the articles are highly compressed in the bag to save space, this may cause a permanent fold line to appear along the bi-fold line of the articles, depending of the material used and the storage time of the articles in bag. Thus it is also considered that the articles may be packaged under a lower compression to avoid this issue, for example corresponding to an in-bag stack height above 80 mm, in particular between 84 mm and 120 mm. The articles may also be packaged tri-folded, as exemplarily disclosed in WO2008/155702 (Hundorf).

The articles may thus also be packaged at a more moderate compression rate than suggested in some of the prior art, in particular at a In Bag Compression Rate of from 5% to 45%, in particular from 10% to 40%. The "In-Bag Compression Rate" as used herein is one minus the height of a stack of 10 folded articles in millimeters, measured while under compression within a ply-bag ("In-Bag Stack Height"), divided by the height of a stack of 10 folded articles of the same type before compression, multiplied by 100; i.e., (1-in-Bag Stack Height/stack height before compression)*100, reported as a percentage. The articles before compression may be typically sampled from the production line between the folding unit and the stack packing unit. The method used to measure the In-Bag Stack Height is described in further details in WO2011/041352 (Weisman) with the Universal Diaper Packaging Tester illustrated in FIG. 19 of WO2008/155702A1 (Hundorf).

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Centrifuge Retention Capacity (CRC)

The CRC measures the liquid absorbed by the superabsorbent polymer particles for free swelling in excess liquid. The CRC is measured according to EDANA method WSP 241.2-05.

Urine Permeability Measurement (UPM) Test method

This method is used to determine the permeability of a swollen hydrogel layer. The results are generally expressed in UPM units equal to $1\times10^{-7}$ cm$^3$·s/g. The Urine Permeability Measurement Test is disclosed in PCT application WO2012/174026A1, incorporated herein by reference.

Thickness Measurement Method

This method is used to measure the thickness of a component of an article or of the article ("sample") itself in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 4.14 kPa of pressure to the sample.

The caliper gauge is mounted with the lower surface of the contact foot in an horizontal plane so that the lower surface of the contact foot contacts the center of the flat horizontal upper surface of a base plate approximately 20 cm×25 cm. The gauge is set to read zero with the contact foot resting on the base plate.

Ruler: Calibrated metal ruler graduated in mm.

Stopwatch: Accuracy 1 second.

Sample preparation: The sample is conditioned at least 24 hours as indicated above.

Measurement procedure: The sample is laid flat with the bottom side, i.e. the side intended to be placed away from the wearer facing down. The point of measurement (if not otherwise indicated the middle of the sample) is carefully drawn on the top side of the sample, taking care not to compress or deform the sample.

The contact foot of the caliper gauge is raised and the sample is placed flat on the base plate of the caliper gauge with the top side of the sample up so that when lowered, the center of the foot is on the marked measuring point.

The foot is gently lowered onto the sample and released (ensure calibration to "0" prior to the start of the measurement). The caliper value is read to the nearest 0.01 mm, 10 seconds after the foot is released.

The procedure is repeated for each sample. Ten samples are measured in this manner for a given material and the average caliper is calculated and reported with an accuracy of one tenth mm.

General

Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a liquid-permeable topsheet, a liquid-impermeable backsheet and an absorbent core disposed between the topsheet and the backsheet, and a liquid management layer disposed between the topsheet and the absorbent core,
   wherein the absorbent core comprises a core wrap having a top layer and a bottom layer enclosing an absorbent layer having absorbent material, the absorbent layer further comprising:
      a non-rectangular central portion having a maximum width, a front edge, a back edge and two longitudinally-extending side edges, wherein each side edge defines a recess along a portion of its length;
      a first side portion present in one of the recess and a second side portion present in the other recess, wherein each side portion comprises a proximal edge relative to the central portion and a curved distal edge further away from the central portion;
   wherein a distance between the two closest points of the curved distal edges of the side portions is 50% to 90% of the maximum width of the nonrectangular central portion;
   wherein the absorbent core further comprises a first folding guide between the first side portion and the central portion, and a second folding guide between the second side portion and the central portion, and when the absorbent core is folded along the folding guides, the central portion and the side portions form a three dimensional basin; and
   wherein the liquid management layer comprises folding guides partially superposed with the folding guides of the absorbent core and partially off-set relative to the folding guides of the absorbent core; and wherein the liquid management layer is disposed between the topsheet and the top layer of the core wrap.

2. The absorbent article of claim 1, wherein the folding guides are areas of the absorbent core substantially free from absorbent material.

3. The absorbent article of claim 2, wherein the top layer of the core wrap is attached to the bottom layer of the core wrap by one or more bonds disposed in the first and/or second folding guides.

4. The absorbent article of claim 1, comprising an auxiliary glue between the top layer and the absorbent layer and/or between the bottom layer and the absorbent layer.

5. The absorbent article of claim 1, wherein the top layer and the bottom layer are longitudinally bonded by a C-wrap seal.

6. The absorbent article of claim 1, wherein each of the side portions has a length as projected on a longitudinal axis of the core which is at least two-tenths of the length of the central portion of the absorbent layer.

7. The absorbent article of claim 1, wherein the folding guides extend to the longitudinally-extending side edges of the central portion of the absorbent layer.

* * * * *